(12) United States Patent
Schrörs et al.

(10) Patent No.: US 11,087,869 B2
(45) Date of Patent: Aug. 10, 2021

(54) MONITORING OPERATING ACTIONS FOR A DIALYSIS APPARATUS

(71) Applicant: Fresenius Medical Care Deutschland GmbH, Bad Homburg (DE)

(72) Inventors: Alexander Schrörs, Frankfurt (DE); Vanessa Nadig, Aachen (DE)

(73) Assignee: Fresenius Medical Care Deutschland GMBH, Bad Homburg (DE)

( * ) Notice: Subject to any disclaimer, the term of this patent is extended or adjusted under 35 U.S.C. 154(b) by 41 days.

(21) Appl. No.: 16/241,646

(22) Filed: Jan. 7, 2019

(65) Prior Publication Data
US 2019/0237180 A1 Aug. 1, 2019

(30) Foreign Application Priority Data

Jan. 29, 2018 (DE) .......................... 102018101893.2

(51) Int. Cl.
| | |
|---|---|
| *G16H 20/17* | (2018.01) |
| *G16H 40/60* | (2018.01) |
| *A61M 1/16* | (2006.01) |
| *A61M 1/30* | (2006.01) |

(52) U.S. Cl.
CPC .......... *G16H 20/17* (2018.01); *A61M 1/1603* (2014.02); *A61M 1/301* (2014.02); *G16H 40/60* (2018.01); *A61M 2205/502* (2013.01); *A61M 2205/52* (2013.01)

(58) Field of Classification Search
CPC ... G16H 20/17; G16H 40/60; A61M 2205/52; A61M 2205/502; A61M 1/301; A61M 1/1603
See application file for complete search history.

(56) References Cited

U.S. PATENT DOCUMENTS

| | | | |
|---|---|---|---|
| 5,402,521 A | 3/1995 | Niida et al. | |
| 5,472,614 A * | 12/1995 | Rossi | A61M 1/16 210/646 |
| 8,006,289 B2 * | 8/2011 | Hinton | H04L 63/08 726/5 |
| 10,173,008 B2 * | 1/2019 | Simpson | G06F 19/3468 |

(Continued)

FOREIGN PATENT DOCUMENTS

AU 2015218864 B2 * 10/2019 .......... A61M 5/1456

OTHER PUBLICATIONS

Patel et al., Continuous User Authentication on Mobile Devices, IEEE Signal Processing Magazine (Year: 2016).*

(Continued)

*Primary Examiner* — Evangeline Barr
*Assistant Examiner* — Jordan L Jackson
(74) *Attorney, Agent, or Firm* — Leydig, Voit & Mayer, Ltd.

(57) ABSTRACT

An operation checking unit for a dialysis apparatus (such as a hemodialysis or peritoneal dialysis machine) is disclosed which comprises an identification unit which is configured to detect a user identity of a user. The operation checking unit also comprises a sensor unit which is configured to detect an operating action of the identified user as an ACTUAL-operation data set, and a processing unit which is configured to compare the detected ACTUAL-operation data set with a DESIRED-operation data set stored in a memory in order to generate a user-specific message in the event of a discrepancy.

14 Claims, 4 Drawing Sheets

(56) References Cited

U.S. PATENT DOCUMENTS

2009/0106605 A1* 4/2009 Kuchibhotla ....... G06F 11/0781
  714/47.2
2009/0275805 A1   11/2009 Lane et al.
2016/0341564 A1* 11/2016 Cheng ................ G01C 21/3641
2017/0065757 A1*  3/2017 Tanenbaum .......... G16H 40/63
2017/0323062 A1   11/2017 Djajadiningrat et al.

OTHER PUBLICATIONS

Halunen et al., Evaluation of user authentication methods in the gadget-free world, 40 Pervasive and Mobile Computing 220-240 (Year: 2017).*
Patel et al., Continuous User Authentication on Mobile Devices, IEEE Signal Processing Magazine (Jul. 2016) (Year: 2016).*
Bio-Plex 200 System, Hardware Instructional Manual, Bio-Rad (Feb. 15, 2017) (Year: 2017).*
System Message Logging, Cisco (Year: 2009).*
German Patent Application No. 10 2018 101 893.2, Office Action (dated Jan. 23, 2019).
International Patent Application No. PCT/EP2019/051859, Search Report (dated Apr. 23, 2019).

* cited by examiner

MONITORING OPERATING ACTIONS FOR A DIALYSIS APPARATUS

CROSS-REFERENCE TO RELATED APPLICATIONS

Priority is claimed to German Patent Application No. DE 102018101893.2, filed on Jan. 29, 2018, the entire disclosure of which is hereby incorporated by reference herein.

FIELD

The present invention relates to the monitoring of the operation of dialysis apparatuses or other medical apparatuses. Exemplary embodiments include an operation checking unit, a medical apparatus having such an operation checking unit, and a method for user-specific monitoring of operating actions during operation of the dialysis apparatus.

BACKGROUND

In clinical practice, a medical apparatus should function in a fault-free manner. The apparatus includes a multiplicity of electronic and/or technical units which likewise should function in a fault-free manner. In order to ensure this, a multiplicity of detectors (such as sensors) are installed in the apparatus and detect a condition of the apparatus with its units and report this to a user in the event of an error via a message via the user interface. For example, if a pump or another component of the apparatus has failed or is no longer functional, this is detected by a corresponding sensor as a fault condition of the apparatus. Therefore, a fault condition of the apparatus can be detected and reported quickly.

However, faults on the apparatus can be produced not only by faulty technical apparatus components but also by an incorrect operation on the part of the user. In the case of hemodialysis treatments, care must be taken, for example, when inserting a heparin syringe for anti-coagulation of blood in the extracorporeal blood circulation system to ensure that the ram of the motor-operated syringe pump is connected in a force-fitting manner to the plunger of the syringe. If this is not the case, the minimal pumping rate of this specific pump can mean that a long period of time elapses in which no heparin is conveyed into the extracorporeal blood. This can result in clotting of the blood in the extracorporeal blood circulation system, whereby the filter can become blocked or in an extreme case clotted blood can even be conveyed back into the vascular system of patient (giving rise to a risk of embolism).

Such a fault can occasionally be life-threatening for the patient.

SUMMARY

In an exemplary embodiment, the present invention provides a medical apparatus. The medical apparatus includes: one or more processors, configured to detect a user identity of a user; and one or more sensors, configured to detect an operating action of the user as an ACTUAL-operation data set. The one or more processors are further configured to compare the detected ACTUAL-operation data set with a DESIRED-operation data set, and to generate a user-specific message in the event of a discrepancy between the detected ACTUAL-operation data set and the DESIRED-operation data set.

In another exemplary embodiment, the present invention provides a method for user-specific monitoring of operating actions during operation of a medical apparatus. The method includes: detecting, by the medical apparatus, a user identity to identify a user; detecting, by the medical apparatus, an operating action of the identified user as an ACTUAL-operation data set; comparing, by the medical apparatus, the detected ACTUAL-operation data set with a stored DESIRED-operation data set; and generating, by the medical apparatus, a user-specific message in the event of a discrepancy.

In yet another exemplary embodiment, the present invention provides a non-transitory computer-readable medium having processor-executable instructions stored thereon for user-specific monitoring of operating actions during operation of a medical apparatus. The processor-executable instructions, when executed, facilitate performance of the following: detecting a user identity to identify a user; detecting an operating action of the identified user as an ACTUAL-operation data set; comparing the detected ACTUAL-operation data set with a stored DESIRED-operation data set; and generating a user-specific message in the event of a discrepancy.

BRIEF DESCRIPTION OF THE FIGURES

Exemplary embodiments of the present invention will be described in even greater detail below based on the exemplary figures. The invention is not limited to the exemplary embodiments. All features described and/or illustrated herein can be used alone or combined in different combinations in embodiments of the invention. Features and advantages of various embodiments of the present invention will become apparent by reading the following detailed description with reference to the attached drawings which illustrate the following.

DETAILED DESCRIPTION

Figure 1:
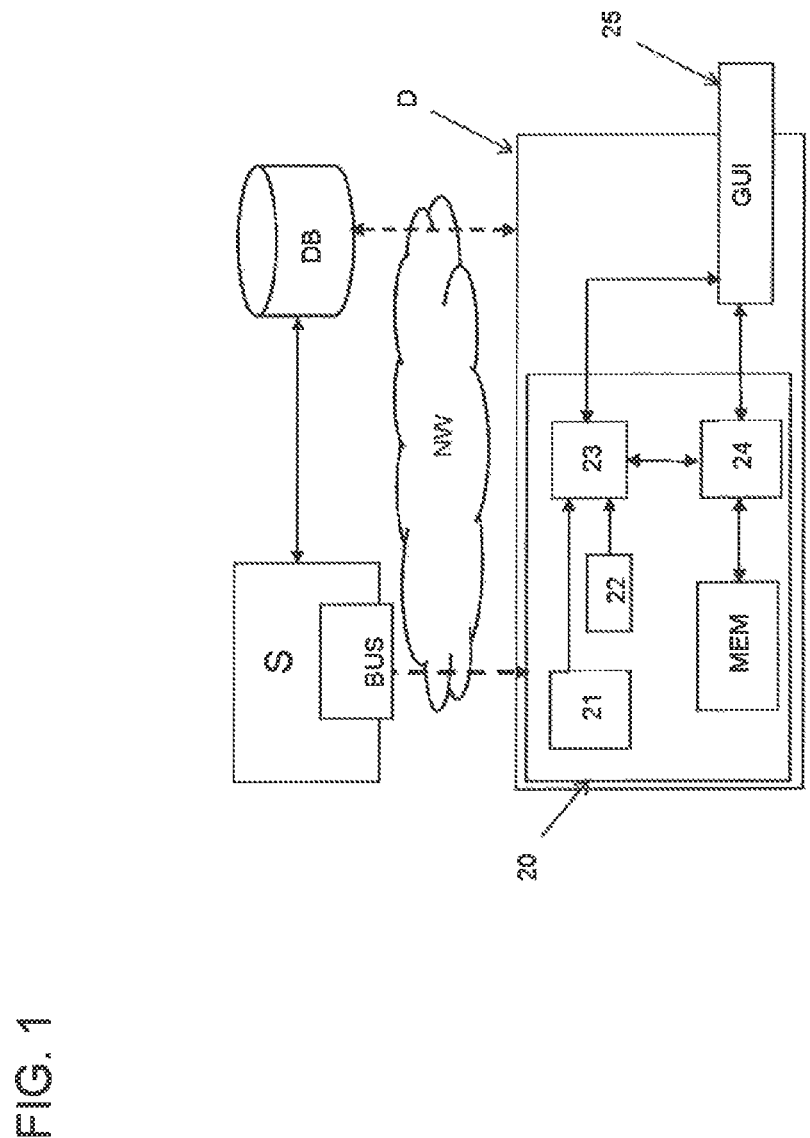
FIG. 1 shows a schematic view of a dialysis apparatus with an operation checking unit according to an exemplary embodiment of the invention.

Monitoring operating actions of users of a medical apparatus may help to ensure freedom from errors and to be able to trigger proactive automatic remedial measures.

Therefore, exemplary embodiments of the present invention improve the reliability of the operation of the apparatus, reduce the number of operating errors, and reduce the time of non-use of the apparatus caused by operating errors. Furthermore, more efficient error handling is provided for the operation of the apparatus.

Exemplary embodiments of the present invention include an operation checking unit, a medical apparatus, and a method.

It will be appreciated that features, advantages or alternatives mentioned herein with respect to an exemplary embodiment may also be applicable to other exemplary embodiments. For example, features of the exemplary methods described herein may also be applicable to exemplary embodiments of the operation checking unit, and vice versa. For example, the corresponding functional features of the method may be embodied by corresponding physical modules such as electronic hardware modules or microprocessor modules, and vice versa. For example, detection of a user identity can be performed by an identification unit which comprises, for example, a camera and performs an optical identification method.

According to a first aspect, the invention relates to an operation checking unit for verifying operating actions of a user for freedom from errors and for user-specific, proactive control of a medical apparatus, such as a dialysis apparatus. To this end, the operation checking unit comprises:

an identification unit which is configured to detect a user identity of a user; this can be performed, for example, during or before an operating action on the medical apparatus;

a sensor unit which is configured to detect an operating action of the identified user as an ACTUAL-operation data set;

a processing unit which is configured to compare the detected ACTUAL-operation data set with a DESIRED-operation data set stored in a memory in order to generate a user-specific message in the event of a discrepancy.

According to exemplary embodiments of the invention, the apparatus operating actions of a specific user for operating the apparatus are detected and evaluated individually in order to initiate control of the apparatus which is adapted to the respective operation of the user and therefore is user-specific, with proactively generated operating instructions and aids for improved and error-free operation of the apparatus. A first user can thus receive different operating instructions than a second user. Via monitoring of the operating actions, the respective user-specific message can be produced even prior to the intended apparatus operating step in order to avoid future operating errors by the user based on operating errors which have been detected in the past.

In the above-mentioned example for inserting the heparin pump, in accordance with an exemplary embodiment of the invention, the depicted fault can be noticed, for example, by monitoring the motor current of the syringe pump which, in the case of a heparin syringe inserted in a force-fitting manner, assumes a different characteristic progression than during an idling cycle of the ram by reason of the counterpressure then present.

In an exemplary embodiment of the invention, the operation checking unit comprises an evaluating unit which is configured to evaluate whether, how often, in which period of time and/or in which operating mode the (respectively current) operating action has been detected, and to provide an evaluation result. Therefore, in an advantageous manner the evaluation result has greater significance and can be tailored more specifically to the operating situation in order to improve the proactive apparatus control with the output of constructive instructions.

In a further advantageous embodiment of the invention, the operation checking unit comprises an output unit which is configured to output the user-specific message, the detected ACTUAL-operation data set, the DESIRED-operation data set and/or an evaluation result. It can be, for example, an operator control panel of the apparatus. Therefore, the user can be provided in a dedicated manner with operating instructions which are helpful specifically to him.

In a further aspect, the invention relates to a medical apparatus, such as a dialysis apparatus, comprising an operation checking unit as described above.

In a further aspect, the invention relates to a method for the user-specific monitoring of operating actions during operation of a medical apparatus, such as a dialysis apparatus, and for the user-specific control of the apparatus. During an operation of the medical apparatus (including activation of the apparatus or start-up, power-up, normal operation, service operation etc.), a user identity is detected followed by an operating action of the identified user as an ACTUAL-operation data set. The detected ACTUAL-operation data set is then directed to configurable data processing, for example, in order to compare it with a stored DESIRED-operation data set in order to generate a user-specific message in the case of a discrepancy.

In a further advantageous embodiment of the invention, the operating action is detected in a first operating phase and the generated user-specific message is output in a second operating phase. In this case, the term "operating phase" refers to an operating phase by the user. This can relate, for example, to a specific procedure on the apparatus or to a sequence of consecutive operating actions. This has, for example, the advantage that, by reason of the previous error monitoring of operating actions for the same procedure (which can include a sequence of operating actions) and for the identical user it has been established that in this case the user has made errors, this information can be used for modified apparatus control. For example, the system can proactively trigger the output of a user instruction in order to inform the user about the specific implementation of the pending operating action and optionally also to inform him that he has previously always made errors when performing the intended operating action. For example, the specific error can be displayed to him, together with the specific implementation. For example, the operating action can also relate to the replacement/installation of a filter. If it has been detected in a previous, earlier operating phase that the user has not rotated the filter but it is necessary for him to do so, he can be made aware of this information prior to the intended apparatus operating measure in order to inform him in advance in a proactive manner about the specific implementation of the operating action. This can considerably reduce the risk of user-specific errors even in advance of performing an action.

In an advantageous embodiment of the invention, the user-specific message is thus output before the operating action is implemented, wherein the user-specific message has been detected from a previous operating phase.

Therefore, in an advantageous embodiment of the invention the generated user-specific message is output even before the respective operating action which causes the message, if in a previous operating phase of the identified user a user-specific message has been generated for the respective operating action. The operating action can be embedded into a sequence of consecutive (predefined, mutually adapted and/or constructive) operating actions. The message can indicate an incorrect operation of the apparatus. The user-specific message can thus be output immediately before a further possibly error-inducing operating action is to be implemented. In this case, the error message is a warning and is intended to be a measure for correcting the user's behavior.

In a further advantageous embodiment of the invention, further metadata, such as a time stamp, are detected with the detection of the operating action. Therefore, a more extensive evaluation of the operating actions can be performed and a highly detailed evaluation result can be provided.

In a further advantageous embodiment of the invention, the user identity is detected by performing an identification process. The identification process can be based on an optical method (camera, eye scan) and/or a biometric method (fingerprint) and/or on an input of key data (password, user name) and/or on the reading-in of data of a mobile data carrier (smart card, pager . . . ). The options listed above can also be used cumulatively. This can increase user identification reliability.

In a further advantageous embodiment of the invention, the user-specific message is output on a monitor of the medical apparatus, such as on a touch-screen monitor. This has the advantage that the user is paying attention to the operating monitor anyway and is not distracted by a further apparatus. Alternatively, the message can also be relayed to other external entities for the purpose of teaching and training the user. The message and the evaluation result can also be relayed to a central server, for example, in order to perform statistical evaluations.

In a further advantageous embodiment of the invention, the user-specific message requires an acknowledgement on the part of the user. This can ensure that the user must also confirm the message before the apparatus can be operated further. Conversely, this can reduce the risk of the message intended to serve as an instruction to the user being overlooked. The acknowledgement is implemented technically by the detection of an acknowledgement signal. The message can indicate an incorrect operation. The message can include operating instructions (as an aid).

In a further advantageous embodiment of the invention, an outputting of the user-specific message can be activated and deactivated. Therefore, on the one hand the detection of the operating actions can be continued and stored in a continued manner and on the other hand the output of the message can be quasi "switched off." This makes the method flexible in use. For example, in emergency situations requiring urgent action the output of instructions and warnings can be switched off so that no acknowledgements even have to be input, whereby the operation can be accelerated. The message can also be triggered automatically after the occurrence of a predefinable event. For instance, rules can be configured and stored, for example, locally in the memory of the apparatus and, for example, establish that a message is provided when an operating error by the user has been detected for the same procedure three times in succession or if the procedure is a safety-critical procedure.

In a further advantageous embodiment of the invention, all of the detected operating actions of all users are aggregated and stored in an itemized manner for each user. This can be performed locally on the apparatus or externally on a central server. The central server or a central unit communicates with the apparatus via data transfer. Alternatively, the processed data, such as the evaluation result, or the messages can be output on the central unit. Therefore, the system can also be used as a training system for training purposes.

In a further advantageous embodiment of the invention, the DESIRED-operation data set is configured for each individual user based on the detected user identity and/or an operating mode. This increases the flexibility of the method.

The operation checking unit is an electronic component. It can be implemented in hardware (as an electronic circuit unit, for example, via an application-specific integrated circuit (ASIC), field-programmable gate array (FPGA) or digital signal processor (DSP), etc.) and/or software and firmware and serves to monitor operating actions which are performed on the apparatus and to ensure correct operation. Furthermore, the operation checking unit serves to control the apparatus by generating and outputting messages or a checking result or processing result adapted specifically to the previously detected operating actions. The operation checking unit is preferably implemented on the apparatus.

The operation checking unit can comprise interfaces to external units (such as a central server).

A dialysis apparatus (such as a hemodialysis apparatus or of a peritoneal dialysis apparatus) is an example of a medical apparatus. Although the exemplary embodiments discussed herein may relate to a dialysis apparatus, it will be appreciated that the principles discussed herein may also be applicable to other medical apparatus, such as other medical computerized apparatuses or (fluid-management) machines or blood-treatment apparatuses which are operated by a user using operating actions which are to be performed on the apparatus.

The operation of the apparatus relates to all operating conditions in which the apparatus is active or activated, such as during powering-up, activation, during a normal operation (such as during the dialysis treatment), service operation, maintenance, shut-down. The list above is not exhaustive. The operation can also relate to a partial operation of only one apparatus component, such as disinfection of the extracorporeal blood circulation system, filling and ventilating the extracorporeal blood circulation system, reaction to alarm messages, end of treatment with blood being returned to the patient, evacuating the extracorporeal blood circulation system, calling-up specific menu points on the user interface (which may be, for example, a graphical user interface (GUI)).

The user identity is an electronic data set which unequivocally denotes the identity of the (current) user on the apparatus. It can switch during apparatus operation and can differ in a first time period from a second time period. The user identity can be a code which unequivocally identifies the user, such as a personal number which is read-in via a data interface. The user identity can also be detected by different technical measures which are based either on different sensors which detect identification data or—as already described above—by reading-in identification data via an interface (for example, a mobile data carrier, such as a smart card, a smart watch, a pager) or by reading-in an NFC code on a data carrier the user carries around with him. In an exemplary embodiment of the invention, sensors which are used can be, for example, visual sensors, such as a camera (CCD camera). The user identity can be detected via biometric methods (such as an optical iris scan and/or detection of a fingerprint on the user interface of the apparatus). An authentication method can also be applied for this purpose, such as the input of a user name and a secret code which identifies the person (for example, a password). The aforementioned identification options can also be used in combination and therefore the reliability of the operation checking unit can be improved.

The ACTUAL-data set and the DESIRED-data set are an electronic data tuple. In a variant of the invention, the ACTUAL- and DESIRED-operation data sets include a plurality of parameters to represent a plurality of sensor values of a predefined sequence. The sensor values can denote a sequence of operating actions by the user on the apparatus (such as, for example, initially starting the disinfection process on the user interface, subsequent opening of the door, disconnecting the hose, . . . ). The operating actions can be detected using different sensors (different oriented optical sensors, switches, proximity sensors etc.). The DESIRED-operation data set can be configured depending upon the application and/or can be read-in by a central administration node. Therefore, it is possible to update the DESIRED-specifications easily and simply or to adapt them to the respective concept.

The message is an electronic notification which is user-specific and indicates the operating actions performed by the user on the apparatus for correctness. Messages include error messages and correctness messages. The error messages can also include further instructions. A message can be directly output locally on the apparatus (for example, on the GUI) and/or can be communicated to an external entity (such as a server) via a data connection in order to perform, for example, further statistical evaluations. An adjustment can be made on the apparatus so that only error messages are output on the apparatus. The message can include metadata which are relevant in the context of the operating action, including apparatus-related metadata (apparatus condition, type of operated component, operating time, operating mode etc.) and operation-related metadata (user's role (patient, doctor, nurse), frequency of the operating error, operating phase (emergency or normal operation)). The message is thus based upon processing on the apparatus. Therefore, the message includes a checking result (as a result of the comparison between the DESIRED- and ACTUAL-operation data sets) and/or a processing result. Therefore, the message can be used as an operating aid.

The error messages can be classified according to a pre-configurable scheme, for instance according to priority or severity. In this case, a distinction can be made between critical and non-critical errors. Non-critical errors have no or only a minor influence upon the patient (for example, uncertainty due to lengthy inputs on the touch-screen). Critical errors are errors which potentially have a significant influence upon the treatment of the patient. If such critical errors occur cumulatively for a specific user, this can be automatically detected in accordance with an exemplary embodiment of the invention and can be reported, for example, to a superior entity (manager, clinic management) by electronic message from the apparatus (or via a data-exchange evaluating unit which does not necessarily have to be located in the medical apparatus). Such a message can then be used as an opportunity to provide the specific user with special training in order to avoid such critical operating errors in future. In an extension of the invention, a stepped escalation of the measures can be initiated in this case in dependence upon the frequency of the operating errors and the significance of the errors.

The output unit is configured to output the message. It is an electronic component. The output unit can be implemented in software or firmware or hardware. In the first case, it can interact with the graphical user interface (GUI) of the apparatus in order to output the message on the interface.

The evaluating unit is configured to evaluate the data detected by the operation checking unit. It is an electronic component and can be implemented in software or firmware or hardware. In the first case, it can be provided as a loadable application. The functionality of the evaluating unit can advantageously also be adapted and updated during operation.

The sensor unit can also comprise a plurality of different sensors, such as optical, acoustic, thermal sensors, movement sensors, gyro sensors, moisture sensors and/or sensors for detecting technical parameters, such as pressure or the position, function and/or location of a component of the apparatus.

In an exemplary embodiment, the present invention provides a computer program product which is, or can be, stored in a memory of a computer or of an electronic or medical apparatus, with a computer program to carry out the method described in more detail above, when the computer program is executed on the computer or the electronic or medical apparatus.

In an exemplary embodiment, the present invention provides a computer program for carrying out all of the method steps of the method described in more detail above when the computer program is executed on a computer or an electronic or medical apparatus. It is thus also possible for the computer program to be stored on a medium which can be read by the computer or the electronic or medical apparatus.

FIG. 1 shows a dialysis apparatus D having an operation checking unit 20 which serves to verify operating actions, which are performed on the dialysis apparatus (hereinunder also referred to in short as apparatus) D, for correctness and to generate operating aids tailored to the individual user. The operation checking unit 20 comprises an identification unit 21 which is configured to detect a user identity of the respective user, and a sensor unit 22 which is configured to detect an operating action of the identified user as an ACTUAL-data set. Furthermore, the operation checking unit 20 comprises a processing unit 23 which is configured to compare the detected ACTUAL-operation data set with a DESIRED-operation data set stored in a memory MEM in order to generate a user-specific message in the event of a discrepancy. The operation checking unit 20 can also comprise an evaluating unit 24 which is configured to evaluate whether, how often, in which period of time and/or in which operating mode the operating action has been detected, and to provide an evaluation result. The evaluation result can likewise be stored locally in the memory MEM. Furthermore, the data (including the evaluation result) detected or ascertained on the operation checking unit 20 can be output on an output unit 25 which can be configured as a GUI. The processing unit 23 can exchange data with a central server S. This can be performed via a bus system BUS and/or via a network NW. The server S can exchange data with the dialysis apparatus D and/or with the operation checking unit 20. Alternatively, the server S can interact directly with the processing unit 23. The server S can exchange data with a database DB in order to store, for example, stored rules for comparing between the ACTUAL-operation data set and the DESIRED-operation data set. Moreover, the DESIRED-operation data set can be stored at this location.

Figure 2:
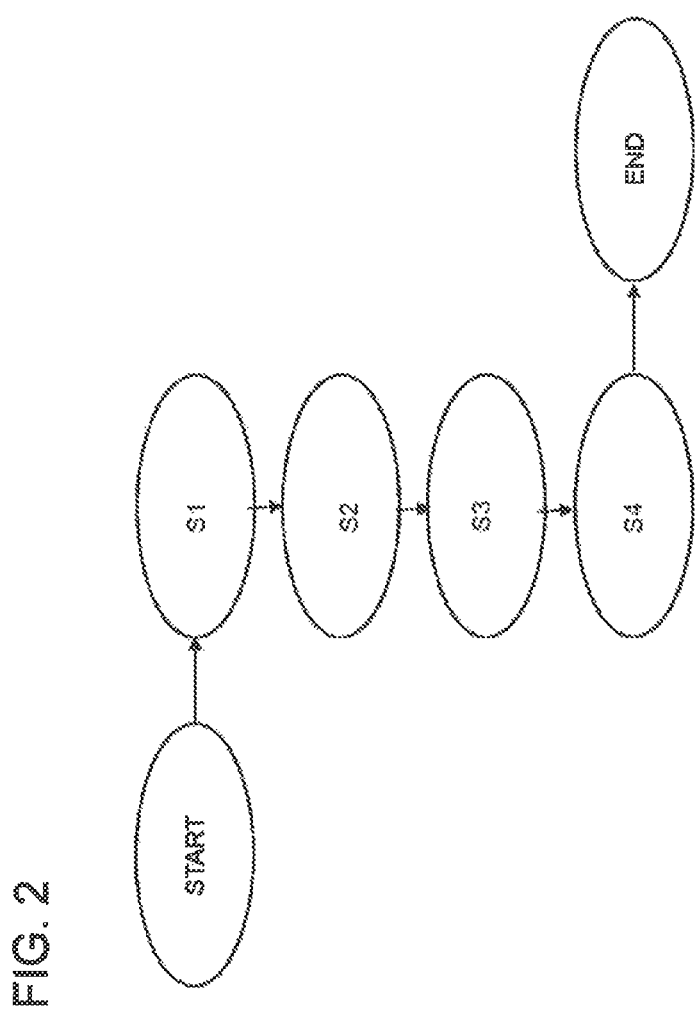
FIG. 2 is an example of a flow diagram for an operating method of a dialysis apparatus with the operation checking unit.

FIG. 2 shows a flow diagram of a method according to an exemplary embodiment of the invention. After start-up, the user identity is detected in an automatic detection process in step S1. Biometric methods and/or other identification processes can be used for this purpose. Identification data can also be read-in via an interface (user data relating to a pager or a smart card, wherein different wireless transmission channels can be used, such as a wireless local area network (WLAN), Bluetooth, near-field communications (NFC), etc.). In step S2, at least one operating action is detected; or a sequence of operating actions is detected. The at least one operating action of the identified user is thus detected as an ACTUAL-operation data set in step S2. In step S3, the detected ACTUAL-operation data set is compared with a stored DESIRED-operation data set. Depending upon the result of the comparison, in step S4, a checking or comparison result is provided in order to generate a user-specific message in the event of a discrepancy. Then, the method can end or can be repeated.

Figure 3:
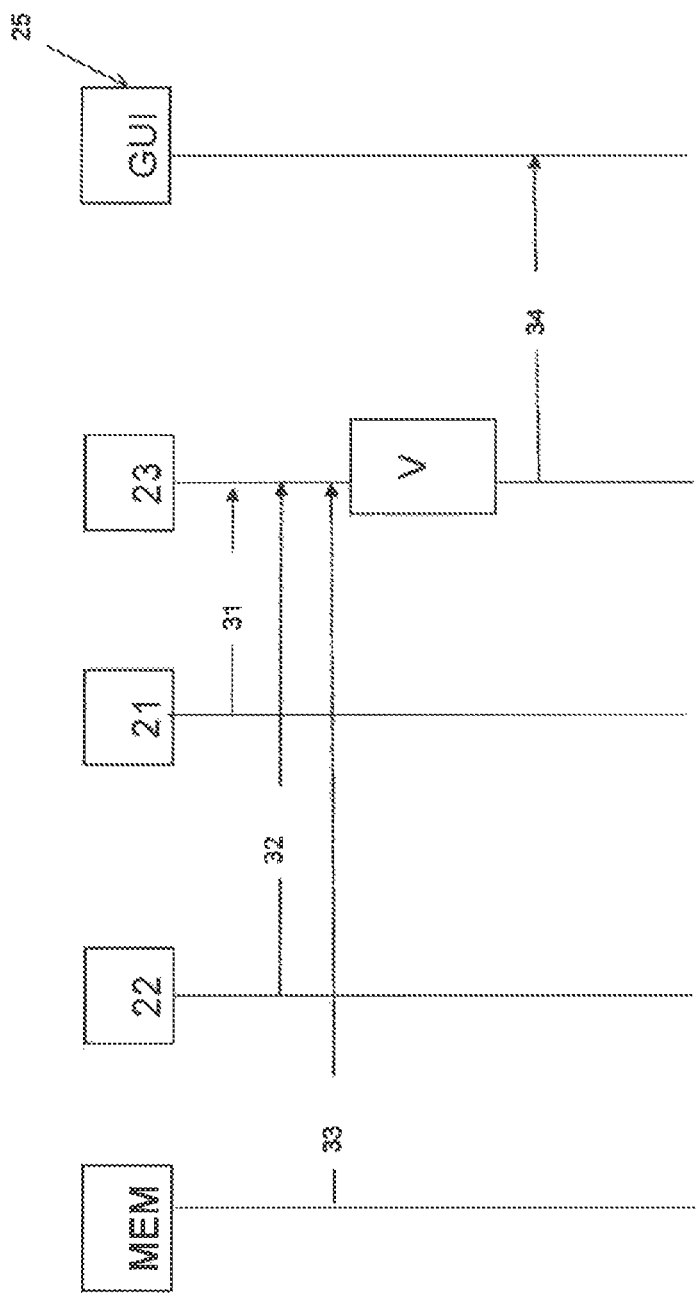
FIG. 3 is an example of a schematic illustration of a data exchange of signals and notifications between the operation checking unit and a user interface of the dialysis apparatus.

FIG. 3 shows an interaction diagram between the electronic modules involved. Identity data 31 which unequivocally identify the user are detected by the identification unit 21 and are communicated to the processing unit 23. The detected ACTUAL-operation data set 32 is detected by the sensor unit 22 during actuation of the operating element BE and is likewise communicated to the processing unit 23. The DESIRED-operation data set 33 is read-out from the memory MEM and is communicated to the processing unit 23. Then, the processing unit 23 has all of the data available for performing data processing V in order to provide a checking result 34. The checking result 34 indicates whether the detected operating action (the ACTUAL-operation data set 32) corresponds to the pre-configured and thus anticipated correct operation (DESIRED-operation data set 33) and is thus correct. The checking result 34 can be displayed on the graphical user interface GUI of the apparatus D. The checking result 34 can include an evaluation result which provides still further statements.

Figure 4:
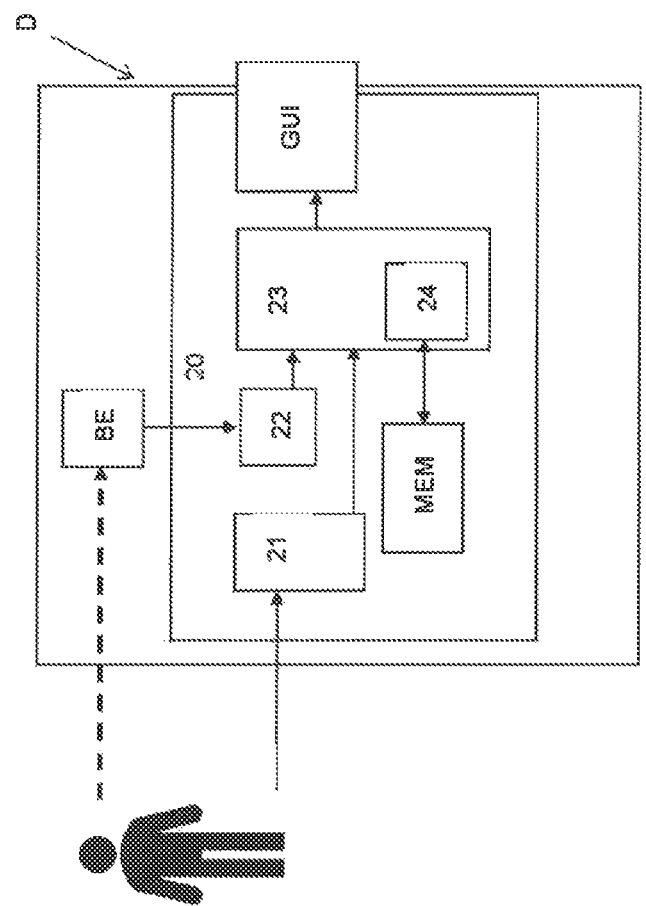
FIG. 4 shows a detailed illustration of the operation checking unit during operation of the dialysis apparatus.

FIG. 4 shows once again in slightly more detail an operation checking unit 20 which can be integrated into a dialysis apparatus D or can be connected thereto. It is illustrated in integrated form in FIG. 4. The operation checking unit 20 is thus configured specifically for the respective dialysis apparatus D or for another medical apparatus D.

The user operates the dialysis apparatus D applying the corresponding operating actions on the apparatus, such as opening the covering doors for changing a filter or for other functions. For this purpose, he operates an operating element BE of the apparatus D. The actuation of the operating element BE is detected automatically via a correspondingly arranged and configured sensor unit 22 comprising at least one sensor. In an advantageous manner, the sensors are arranged distributed on different operating assemblies and comprise a multiplicity of different sensor types (for measuring a position, a movement of a component or for measuring a pressure or current, voltage or other technical parameters). The identity of the user is likewise detected via the corresponding identification unit 21. The identification data set detected by the identification unit 21 is relayed to the processing unit 23. Likewise, the sensor data which have been detected by the sensor unit 22 in order to detect an operating action by the identified user as an ACTUAL-operation data set are transmitted to the processing unit 23. The processing unit 23 processes the communicated data, for example, by comparing the detected ACTUAL-operation data set to the DESIRED-operation data set in order, in the event of a discrepancy, to generate the user-specific message which can then be output on the GUI of the apparatus D.

By incorporating the operation checking unit 20 in accordance with the invention into the medical system, user-specific operating characteristics can be automatically recognized and processed. For instance, user-specific messages and error messages can also be output proactively. Thus, prior to possibly repeated incorrect operations, assistance can be provided to prevent an error situation from occurring at all.

Therefore, the apparatus can be specifically "adjusted" to the user. The apparatus can automatically be configured in a user-specific manner, in that future operating actions are suggested and assistance offered on the basis of operating actions by the user which are detected in at least one previous operating time period. This provides a user-specific approach for avoiding errors.

Since each user makes different errors, the heuristics to be applied in the operation checking unit 20 are user-specific. The user-specific or user-typical operating behavior is detected in a first operating phase. The calculated message can be output in a second (planned future) operating phase.

The operating behavior is detected preferably within the apparatus. The data collected thereby are stored. The collected data (aggregated ACTUAL-operation data sets) are stored preferably locally (within the apparatus) and are updated each time the user performs an operating action. For storage purposes, it is possible to use a list structure as a data structure which is to be represented hereinunder:

| Operating action | User error | Message number | Time of day | Frequency |
|---|---|---|---|---|
| TPE | filter not rotated during preparation | #5312 | 23:12 | 5 |
| CiCa-CVVHDF | filter bag clamp closed after bag change | #5515 | 09:25 | 10 |
| TPE | coupling test failed | #5315 | 20:55 | 3 |

The frequency (last column) can be calculated in relation to a predefinable time period. TPE stands for Therapeutic Plasma Exchange and CVVHD relates to continuous venovenous hemodialysis. Ci-Ca® dialysates are used in citrate anticoagulation.

The locally detected operating action data of the user (the collected ACTUAL-operation data sets) can be further processed locally and/or at another location (for example, centrally), via, for example, a statistical analysis in order to be able to predict probabilities for typical treatment errors.

For example, if it is detected that the detected messages change over the course of time (for example, because specific errors are no longer being made), then this change is likewise automatically detected and implemented for the purpose of apparatus control. For instance, during set-up of the apparatus, messages can be configured to no longer be output and displayed when they have no longer been detected over a pre-configurable time period during which errors are not made (for example, not in the last 5 or 10 operations or in a time period of 1 day or 1 week).

As shown in the example table above, a time of day can also be detected for the operating action. If the collected data indicate, for example, that a specific error (TPE in the example) is always made during the night and not during the day (or in specific time periods), then the apparatus can be activated automatically in such a way that the message for error avoidance is output only during the night and not during the day (only in the specific time periods).

The message can also include an indication relating to the source of the error and its effect(s).

A fixed, predefinable structure is preferably used for the messages. This serves to make the messages distinguishable from other apparatus messages in order to configure the operation of the apparatus to be easier and more efficient. The messages can have, for example, a specific appearance (look and feel).

It is noted that the description of the invention and the exemplary embodiments are non-limiting with respect to specific physical implementations of the invention. Features explained and illustrated in conjunction with exemplary embodiments of the invention can be provided in different combinations in accordance with the invention in order to achieve the advantageous effects thereof at the same time. Therefore, it is, for example, likewise within the scope of the invention to provide other operating or control elements of the medical apparatus for outputting the processing result 34 alternatively or cumulatively with respect to the graphical user interface 25. The elements can also be, for example, external output apparatuses. It will be appreciated that the invention can be used not just for dialysis apparatuses but also for other medical apparatuses D in which a correct operation has to be verified. If no correct operation is determined, a processing result 34 is to be generated and optionally output.

Furthermore, the components of the medical system for monitoring operating actions and the operation checking unit 20 can be provided in a manner distributed to a plurality of physical products.

It will be appreciated that the execution of the various machine-implemented processes and steps described herein may occur via the execution, by one or more respective processors, of processor-executable instructions stored on a tangible, non-transitory computer-readable medium, such as random access memory (RAM), read-only memory (ROM), programmable read-only memory (PROM), and/or another electronic memory mechanism. Thus, for example, operations performed by the dialysis apparatus, the operation checking unit, the identification unit, the sensor unit, the processing unit, the evaluating unit, the output unit, the central server, the database, etc., as discussed herein may be carried out according to instructions stored on and/or applications installed on one or more respective computing devices.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A medical apparatus, comprising:
    one or more processors configured to detect a user identity of a user; and
    one or more sensors configured to detect, during a first operating phase corresponding to a first iteration of a user action to be performed by the user on a component of the medical apparatus, an operating action of the user performed on the component of the medical apparatus as an ACTUAL-operation data set;
    wherein the medical apparatus is a dialysis machine comprising a syringe pump;
    wherein the user action to be performed by the user on a component of the medical apparatus corresponds to insertion of a heparin syringe in connection with the syringe pump;
    wherein the one or more sensors are further configured to monitor a motor current of the syringe pump; and
    wherein the one or more processors are further configured to:
        detect a user error based on comparing the detected ACTUAL-operation data set with a DESIRED-operation data set and determining a discrepancy between the detected ACTUAL-operation data set and the DESIRED-operation data set, wherein the detected user error corresponds to the heparin syringe being inserted incorrectly relative to the syringe pump, and the detected user error is detected based on evaluating a progression of the motor current of the syringe pump;
        cause the detected user error to be stored in a manner wherein the detected user error is associated with the user;
        classify the detected user error with regard to whether the detected user error corresponds to a critical user error or a non-critical user error;
        in response to detecting a number of critical user errors for the user, output a report related to the number of critical user errors for the user; and
        during a second operating phase corresponding to a second iteration of the user action to be performed by the user on the component of the medical apparatus, and based on the stored detected user error associated with the user, proactively trigger output of a user-specific message to provide the user with instructional information regarding the action to be performed by the user on the component of the medical apparatus prior to the user performing an operating action on the component of the medical apparatus during the second operating phase.

2. A method for user-specific monitoring of operating actions during operation of a dialysis machine, the method comprising:
    detecting, by the dialysis machine, a user identity to identify a user;
    detecting, by the dialysis machine via one or more sensors of the dialysis machine, during a first operating phase corresponding to a first iteration of a user action to be performed by the user on a component of the dialysis machine, an operating action of the identified user performed on the component of the dialysis machine as an ACTUAL-operation data set, wherein the user action to be performed by the user on a component of the dialysis machine corresponds to insertion of a heparin syringe in connection with a syringe pump of the dialysis machine;
    monitoring, by the dialysis machine via the one or more sensors of the dialysis machine, a motor current of the syringe pump;
    detecting, by the dialysis machine, a user error based on comparing the detected ACTUAL-operation data set with a stored DESIRED-operation data set and determining a discrepancy between the detected ACTUAL-operation data set and the DESIRED-operation data set, wherein the detected user error corresponds to the heparin syringe being inserted incorrectly relative to the syringe pump, and the detected user error is detected based on evaluating a progression of the motor current of the syringe pump;

causing, by the dialysis machine, the detected user error to be stored in a manner wherein the detected user error is associated with the user;

classifying, by the dialysis machine, the detected user error with regard to whether the detected user error corresponds to a critical user error or a non-critical user error;

in response to detecting a number of critical user errors for the user, outputting, by the dialysis machine, a report related to the number of critical user errors for the user; and during a second operating phase corresponding to a second iteration of the user action to be performed by the user on the component of the dialysis machine, and based on the stored detected user error associated with the user, proactively triggering, by the dialysis machine, output of a user-specific message to provide the user with instructional information regarding the action to be performed by the user on the component of the dialysis machine prior to the user performing an operating action on the component of the dialysis machine during the second operating phase.

3. The method according to claim 2, wherein the user-specific message further includes information regarding one or more previous errors made by the user when performing the user action to be performed by the user on the component of the dialysis machine.

4. The method according to claim 2, wherein detection of the operating action includes detection of metadata.

5. The method according to claim 4, wherein the metadata includes a time stamp.

6. The method according to claim 2, wherein the user identity is detected by performing an identification process which is based on an optical method and/or a biometric method and/or input of key data and/or reading-in data of a mobile data carrier.

7. The method according to claim 2, wherein the user-specific message is output on a monitor of the dialysis machine.

8. The method according to claim 7, wherein the monitor is a touch screen monitor.

9. The method according to claim 2, wherein the user-specific message requires an acknowledgement on the part of the user.

10. The method according to claim 2, wherein outputting of the user-specific message is activated or deactivated automatically after the occurrence of a predefinable event or a predefinable time period.

11. The method according to claim 2, wherein detected operating actions of a plurality of users are aggregated and are output and/or stored in an itemized manner for each user.

12. The method according to claim 11, wherein the DESIRED-operation data set is configured for each individual user based on the detected user identity and/or an operating mode.

13. The medical apparatus according to claim 1, wherein the stored detected user error comprises an operating action parameter, a user error parameter, a message number parameter, a time parameter, and a frequency parameter.

14. A medical apparatus, comprising:
one or more processors configured to detect a user identity of a user; and
one or more sensors configured to detect, during a first operating phase corresponding to a first iteration of a user action to be performed by the user on a component of the medical apparatus, an operating action of the user performed on the component of the medical apparatus as an ACTUAL-operation data set;
wherein the medical apparatus is a dialysis machine comprising a filter;
wherein the user action to be performed by the user on a component of the medical apparatus corresponds to replacing or installing the filter; and
wherein the one or more processors are further configured to:
detect a user error based on comparing the detected ACTUAL-operation data set with a DESIRED-operation data set and determining a discrepancy between the detected ACTUAL-operation data set and the DESIRED-operation data set, wherein the detected user error corresponds to the user failing to rotate the filter;
cause the detected user error to be stored in a manner wherein the detected user error is associated with the user;
classify the detected user error with regard to whether the detected user error corresponds to a critical user error or a non-critical user error;
in response to detecting a number of critical user errors for the user, output a report related to the number of critical user errors for the user; and
during a second operating phase corresponding to a second iteration of the user replacing or installing a filter for the dialysis machine, and based on the stored detected user error associated with the user, proactively trigger output of a user-specific message to provide the user with instructional information regarding rotation of the filter prior to the user replacing or installing the filter during the second operating phase.

\* \* \* \* \*